United States Patent
Kim et al.

(10) Patent No.: US 11,976,338 B2
(45) Date of Patent: May 7, 2024

(54) METHOD OF MANUFACTURING CORONAVIRUS DIAGNOSTIC KIT, VIRUS DIAGNOSTIC KIT MANUFACTURED THEREBY AND METHOD OF DIAGNOSING CORONAVIRUS USING THE SAME

(71) Applicant: OSANG HEALTHCARE CO., LTD., Anyang-si (KR)

(72) Inventors: Joo Hyung Kim, Suwon-si (KR); Go Woon Cha, Incheon (KR)

(73) Assignee: OSANG HEALTHCARE CO., LTD., Anyang-si (KR)

( * ) Notice: Subject to any disclaimer, the term of this patent is extended or adjusted under 35 U.S.C. 154(b) by 317 days.

(21) Appl. No.: 17/274,748

(22) PCT Filed: Apr. 22, 2020

(86) PCT No.: PCT/KR2020/005337
§ 371 (c)(1),
(2) Date: Mar. 9, 2021

(87) PCT Pub. No.: WO2021/215556
PCT Pub. Date: Oct. 28, 2021

(65) Prior Publication Data
US 2023/0147691 A1 May 11, 2023

(51) Int. Cl.
*C12Q 1/70* (2006.01)
*C12Q 1/6806* (2018.01)
*C12Q 1/6851* (2018.01)

(52) U.S. Cl.
CPC ........... *C12Q 1/701* (2013.01); *C12Q 1/6806* (2013.01); *C12Q 1/6851* (2013.01)

(58) Field of Classification Search
CPC .... C12Q 1/6806; C12Q 1/6851; C12Q 1/701; C12Q 1/70; C12Q 1/6844; C12Q 1/6853; C12Q 1/686; C12Q 1/6858; C12Q 1/6862; C12Q 1/6865; C12Q 1/6869; C12Q 1/6876; C12Q 2500/00; C12Q 2520/00; C12Q 2521/00; C12Q 2522/00; C12Q 2531/00; C12Q 2537/00; C12Q 2543/00; C12Q 2547/00; C12Q 2545/00; C12Q 2560/00; C12Q 2561/00; C12Q 2563/00; C12Q 2565/00; C12Q 2600/00; C12Q 3/00; C12Q 2304/00; C12Q 1/6867; C12Q 1/6813; C12Q 1/6811; C12Q 1/6809; C12Q 1/68; C12Q 1/66; C12Q 1/02; C12Q 1/00
See application file for complete search history.

(56) References Cited

PUBLICATIONS

International Search Report and Written Opinion of corresponding PCT/KR2020/005337, dated Jan. 19, 2021, pp. 1-12.
"GeneFinder COVID-19 Plus RealAmp Kit," Material No. MFK-45, Apr. 18, 2020, pp. 1-19, (URL: https://www.fda.gov/media/137116/download).
"GeneFinder COVID-19 Plus RealAmp Kit CE-IVD," Mar. 17, 2020, pp. 1-21, (URL: https://cdn2.hubspot.nel/hubfs/7408315/COVID19/2-OSANG%20GeneFinder%20Sales%20Material/OHC_COYID19_MD_kit_INTRODUCTION.pdf).
URL: https://www.doctorsnews.co.kr/news/articleView.html?idxno=134345) Apr. 21, 2020 (On Order).
Rao, Arundhati, "Development and evaluation of two SARS-COV-2 RT-PCT laboratory developed tests on the ARIES automated, sample-to-answer, real-time PCR system," White Health, Mar. 2020, pp. 1-8 (On Order).
Corman, Victor M., "Detection of 2019 novel coronavirus (2019-nCOV) by real-time RT-PCR," Eurosurveillance, Article 2000045, Jan. 23, 2020/Mar. 25, 2020, pp. 1-8 (On Order).
Wang, Changtai, "The establishment of reference sequence for SARS-COV-2 and variation analysis," Journal of Medical Virology, vol. 92, No. 6, Mar. 13, 2020, pp. 667-674 (On Order).
Doctor's News, "Seegen, Achieved 10 Million Test Exports of Corona 19 Diagnosis Reagents," (URL: https://www.doctorsnews.co.kr/news/articleView.html?idxno=134345) Apr. 21, 2020, 4 pages.
Rao, Arundhati, "Development and evaluation of two SARS-COV-2 RT-PCR laboratory developed tests on the ARIES automated, sample-to-answer, real-time PCR system," White Health, Mar. 2020, pp. 1-8.
Corman, Victor M., "Detection of 2019 novel coronavirus (2019-nCOV) by real-time RT-PCR," Eurosurveillance, Article 2000045, Jan. 23, 2020/Mar. 25, 2020, pp. 1-8.
Wang, Changtai, "The establishment of reference sequence for SARS-COV-2 and variation analysis," Journal of Medical Virology, vol. 92, No. 6, Mar. 13, 2020, pp. 667-674.

*Primary Examiner* — Bao Q Li
(74) *Attorney, Agent, or Firm* — Lewis Roca Rothgerber Christie LLP

(57) ABSTRACT

Provided are a method of manufacturing a coronavirus diagnostic kit, which includes preparing a one-component primer/probe mixture by mixing a primer set including a primer pair consisting of base sequences of SEQ ID NOs: 1 and 2, a primer pair consisting of base sequences of SEQ ID NOs: 3 and 4, a primer pair consisting of base sequences of SEQ ID NOs: 5 and 6, and a primer pair consisting of base sequences of SEQ ID NOs: 7 and 8; and a probe consisting of a base sequence of SEQ ID NO: 9, a probe consisting of a base sequence of SEQ ID NO: 10, a probe consisting of a base sequence of SEQ ID NO: 11, and a probe consisting of a base sequence of SEQ ID NO: 12, a coronavirus diagnostic kit manufactured using the same, and a method of diagnosing coronavirus using the same.

6 Claims, No Drawings
Specification includes a Sequence Listing.

METHOD OF MANUFACTURING CORONAVIRUS DIAGNOSTIC KIT, VIRUS DIAGNOSTIC KIT MANUFACTURED THEREBY AND METHOD OF DIAGNOSING CORONAVIRUS USING THE SAME

CROSS-REFERENCE TO RELATED APPLICATION(S)

This application is a U.S. National Phase Patent Application of International Application Number PCT/KR2020/005337, filed on Apr. 22, 2020, the entire contents of which is incorporated herein by reference.

STATEMENT REGARDING PRIOR DISCLOSURES BY THE INVENTOR OR A JOINT INVENTOR UNDER 37 CFR 1.77(b)(6)

A document (titled "GeneFinder™ COVID-19 Plus RealAmp Kit," hereinafter referred to as "Document 1") describing one or more embodiments of the present disclosure was submitted to the U.S. Food and Drug Administration ("the FDA") in connection with a submission for an emergency use authorization of an embodiment of a kit of the present disclosure by OSANG HEALTHCARE CO., LTD., and Document 1 was published on Mar. 17, 2020, on the FDA website homepage. Additionally, a document (titled "GeneFinder™ COVID-19 Plus RealAmp Kit CE-IVD," hereinafter referred to as "Document 2") was published by OSANG HEALTHCARE CO., LTD's overseas agency on Apr. 18, 2020. The contents of Document 1 and Document 2 were obtained from the present inventors, Joo Hyung Kim and Go Woon Cha. Copies of Document 1 and Document 2 are provided with a concurrently filed Information Disclosure Statement pursuant to the guidance of 78 Fed. Reg. 11076 (Feb. 14, 2013).

SEQUENCE LISTING

The instant application contains a Sequence Listing submitted in ASCII format via EFS-Web and is incorporated herein by reference in its entirety. Said ASCII copy, which was last modified on Nov. 3, 2022, is named "AJP20728PCTUS-Sequence listing.txt", and is 4,096 bytes in size.

TECHNICAL FIELD

The present invention relates to a method of manufacturing a coronavirus diagnostic kit, a coronavirus diagnostic kit manufacturing the same, and a method of diagnosing coronavirus using the same.

BACKGROUND ART

Recently, due to the coronavirus pandemic, the number of confirmed cases and deaths is exploding. Coronavirus (SARS-CoV-2; Severe Acute Respiratory Syndrome Coronavirus 2) causing Coronavirus Disease-19 (COVID-19) not only spreads very quickly between contacts, but also has no effective therapeutics or vaccines. Therefore, the only way to prevent the spread of further infection is identifying people with coronavirus as early as possible.

To this end, a coronavirus diagnostic kit using a real-time polymerase chain reaction (PCR) is used. The diagnostic kit using real-time PCR is based on a method of amplifying and confirming only a specific gene by extracting viral RNA from a collected sample and then performing reverse transcription of the extracted viral RNA.

To increase the reliability of virus diagnosis, for the purpose of amplifying a specific site of viral RNA, a plurality of primer pairs targeting viral RNA and probes corresponding thereto are required. Typically, a diagnostic kit was used to diagnose a target virus after primer pairs specifically binding to a target gene and probes corresponding thereto were put into separate containers. However, in this case, a user has no choice but to handle multiple containers at the same time, so there is difficulty in use. Particularly, in the case of virus diagnostic kits, such difficulty can be even greater since the amount of a sample used increases and contamination is frequently caused during testing.

However, if a plurality of primer pairs and probes are randomly mixed, there is a problem that analysis reliability may be degraded during virus diagnosis. As known to those of ordinary skill in the art, viral RNA consists of a sequence of several bases, and thus a test result may vary depending on which site of the base sequence is specifically amplified. In addition, according to the amplification site of viral RNA, interference between primers may occur, leading to a problem in reliability during virus diagnosis.

DISCLOSURE

Technical Problem

The present invention is directed to providing a method of manufacturing a coronavirus diagnostic kit that can conveniently detect coronavirus.

The present invention is also directed to providing a method of manufacturing a coronavirus diagnostic kit with high reliability for coronavirus analysis, which even includes a plurality of primer pairs and probes.

Technical Solution

One aspect of the present invention provides a method of manufacturing a coronavirus diagnostic kit.

The method of manufacturing a coronavirus diagnostic kit includes preparing a one-component primer/probe mixture by mixing a primer set including a primer pair consisting of base sequences of SEQ ID NOs: 1 and 2, a primer pair consisting of base sequences of SEQ ID NOs: 3 and 4, a primer pair consisting of base sequences of SEQ ID NOs: 5 and 6, and a primer pair consisting of base sequences of SEQ ID NOs: 7 and 8; and a probe consisting of a base sequence of SEQ ID NO: 9, a probe consisting of a base sequence of SEQ ID NO: 10, a probe consisting of a base sequence of SEQ ID NO: 11, and a probe consisting of a base sequence of SEQ ID NO: 12.

In one embodiment, the method may further include preparing a composition which includes a plasmid containing RdRp gene of the coronavirus, a plasmid containing N gene of the coronavirus, a plasmid containing E gene of the coronavirus, and a plasmid containing human RNase P gene.

The one-component primer/probe mixture may be prepared in a container separate from the composition including the plasmids.

The coronavirus diagnostic kit prepared by the above-described method may be used in real-time PCR.

Another aspect of the present invention is a coronavirus diagnostic kit.

The coronavirus diagnostic kit is prepared by the method of manufacturing a coronavirus diagnostic kit of the present invention.

Still another aspect of the present invention is a method of diagnosing coronavirus.

The method of diagnosing coronavirus includes using the coronavirus diagnostic kit of the present invention.

Advantageous Effects

The present invention provides a method of manufacturing a coronavirus diagnostic kit, which enables a user to conveniently detect coronavirus.

The present invention provides a method of manufacturing a coronavirus diagnostic kit with a high reliability for coronavirus analysis, which even includes a plurality of primer pairs and probes.

Modes of the Invention

Embodiments of the present invention will be described in detail with reference to the accompanying drawings so that those of ordinary skill in the art can easily carry out the present invention. However, the present invention may be implemented in a variety of different forms, and is not limited to the embodiments described herein. In addition, terms to be described below are terms defined in consideration of functions of the present invention, which may be used as other terms according to the intention or custom of a measurer or operator. Therefore, the definition should be determined based on the contents of the entire specification including the claims.

The present invention allows a user to conveniently detect coronavirus. To this end, a method of manufacturing a coronavirus diagnostic kit according to one embodiment of the present invention, to confirm coronavirus infection, includes preparing a one-component primer/probe mixture by mixing a primer set including a primer pair consisting of base sequences of SEQ ID NOs: 1 and 2, a primer pair consisting of base sequences of SEQ ID NOs: 3 and 4, a primer pair consisting of base sequences of SEQ ID NOs: 5 and 6, and a primer pair consisting of base sequences of SEQ ID NOs: 7 and 8; and a probe consisting of a base sequence of SEQ ID NO: 9, a probe consisting of a base sequence of SEQ ID NO: 10, a probe consisting of a base sequence of SEQ ID NO: 11, and a probe consisting of a base sequence of SEQ ID NO: 12.

The term "diagnosis" used herein refers to confirming a pathological condition. For the purpose of the present invention, diagnosis is to check the presence or absence of the expression of a gene specific for conventional various coronaviruses to confirm the occurrence of a disease caused by coronavirus and prognosis in treatment with an antiviral agent after the onset thereof.

The term "primer" used herein refers to a short nucleic acid sequence having a free 3' hydroxyl group, which is able to form a base pair with a complementary template and serves as a starting point for replication of a template strand. A primer may initiate DNA synthesis in the presence of a reagent for polymerization (DNA polymerase or reverse transcriptase) with a suitable buffer solution at a suitable temperature and four different types of dNTPs. According to the present invention, the primer preferably consists of forward and reverse nucleic acids each having a sequence of approximately 20 nucleotides.

The term "coronavirus" used herein may refer to a novel coronavirus (SARS-CoV-2).

In the present invention, instead of independently containing primer pairs and probes required for detecting coronavirus in separate containers, a specific combination of primer pairs and probes, which amplify only specific sites in a full-length base sequence of the coronavirus through PCR, is selected, and mixed as a one-component type. The "one-component type" used herein means containing a primer and a probe in one container.

When the primer pair and/or probes are added to separate containers, there is a high possibility of contamination, and more containers are needed as the number of primer pairs and/or probes increase(s). However, even if primer pairs and probes randomly recognizing specific sites in the full-length base sequence of coronavirus are mixed, it may be difficult to identify a gene of coronavirus, or problems can arise with analytic specificity, analytic sensitivity, reproducibility, repeatability and interference. On the other hand, in the present invention, it was intended to prevent problems in analytic specificity, analytic sensitivity, reproducibility, repeatability and interference when a target gene of coronavirus is identified by selecting primer pairs and probes in combination of specific sequences to be described below and mixing them in a one-component mixture including all of the primers and probes.

Specifically, in the present invention, as genes that can differentiate coronavirus from other types of viruses, an RNA-dependent RNA polymerase gene (RdRp gene), a nucleus protein gene (N gene), and or an envelope protein gene (E gene) of coronavirus were used.

More specifically, in the present invention, a forward nucleic acid amplifying the RdRp gene of coronavirus (SEQ ID NO: 1), and a reverse nucleic acid amplifying the RdRp gene of coronavirus (SEQ ID NO: 2) are included.

More specifically, in the present invention, a forward nucleic acid amplifying the N gene of coronavirus (SEQ ID NO: 3), and a reverse nucleic acid amplifying the N gene of coronavirus (SEQ ID NO: 4) are included.

More specifically, in the present invention, a forward nucleic acid amplifying the E gene of coronavirus (SEQ ID NO: 5), and a reverse nucleic acid amplifying the E gene of coronavirus (SEQ ID NO: 6) are included.

Meanwhile, in the present invention, to provide criteria for determining the effectiveness of an RNA extraction process in the identification of coronavirus genes, and detect errors in nucleic acid extraction and amplification, as internal control primers, a forward nucleic acid amplifying a human RNase gene (RNase P gene) (SEQ ID NO: 7), and a reverse nucleic acid amplifying the human RNase P gene (SEQ ID NO: 8) are additionally used. These sequences of SEQ ID NOs: 7 and 8 may prevent problems in analytic specificity, analytic sensitivity, reproducibility, repeatability and interference during identification of a coronavirus gene even when combined with the primer pair of SEQ ID NOs: 1 and 2, the primer pair of SEQ ID NOs: 3 and 4, and the primer pair of SEQ ID NOs: 5 and 6 in the one-component type.

The primers may include additional characteristics without changing the basic properties of primers acting as a starting point of DNA synthesis. In addition, the primer nucleic acid sequences of the present invention may include markers that can be directly or indirectly detected by spectroscopic, photochemical, biochemical, immunochemical or chemical means when needed. Examples of the markers may be enzymes, radioactive isotopes, fluorescent molecules, or chemical groups.

In the present invention, a probe is used to detect a specific gene of coronavirus. Since the inventors can monitor, in real-time, an increase in amplified product when the amplified product is detected by real-time PCR, DNA and RNA can be exactly quantified, analyzed quickly and easily because electrophoresis is not required, have less risk of contamination, and there are no problems in analytic specificity, analytic sensitivity, reproducibility, repeatability and interference even when mixing with the above-described base sequences of SEQ ID NOs: 1 and 2, base sequences of SEQ ID NOs: 3 and 4, base sequences of SEQ ID NOs: 5 and 6, and base sequences of SEQ ID NOs: 7 and 8 in the identification of a coronavirus gene.

The term "probe" used herein refers to a nucleic acid fragment of DNA or RNA that is able to achieve specific binding with a complementary base sequence, and corresponds to several to hundreds of bases. The probe may be labeled to identify the presence or absence of a specific base sequence. The probe may be formed as an oligonucleotide probe, a single-stranded DNA probe, a double-stranded DNA probe, or an RNA probe. In addition, to perform real-time PCR, a fluorescence-labeled probe may be used. More specifically, when a TaqMan probe is used, a oligonucleotide in which the 5' end is modified with a fluorescent material, and the 3' end is modified with a quencher material is added to a PCR reaction solution.

In one embodiment, the fluorescent material may be FAM, JOE, Texas Red, Cy5, Cal Red 610, VIC, or Quaser 670, but the present invention is not particularly limited thereto.

In one embodiment, the quencher material may be a black hole quencher (BHQ) or a SFC quencher (SFCQ), but the present invention is not particularly limited thereto.

More specifically, in the present invention, a probe detecting RdRp gene of coronavirus (SEQ ID NO: 9), a probe detecting N gene of coronavirus (SEQ ID NO: 10), a probe detecting E gene of coronavirus (SEQ ID NO: 11) and a probe detecting human RNase P gene (SEQ ID NO: 12) are included.

The primer and/or probe of the present invention may be chemically synthesized by a phosphoramidite solid support method or another widely known method. These nucleic acid sequences may be modified using various means known in the art. Examples of such modification may include methylation, capping, and substitution with a nucleotide homolog.

The above-described primer/probe mixture may further include a buffer generally used by those of ordinary skill in the art to store and maintain a primer or probe (e.g., a TE-buffer).

Each of the above-described primers and probes may be included at 50 to 150 pmol per 1 μl of the above-described mixture, but the present invention is not particularly limited thereto.

The above-described primer/probe mixture may be contained and stored in a tube or container such as another suitable ampoule.

The method of the present invention may further include preparing a composition for performing real-time PCR. The composition may be stored in a separate container from the above-described primer/probe mixture.

The composition may include a reverse transcriptase for synthesizing complementary DNA (cDNA) from RNA which is a coronavirus gene, a Taq polymerase for amplifying cDNA, a reaction buffer (whose pH and magnesium concentration are variously adjusted), deoxynucleotides (dNTPs; dATP, dTTP, dGTP and dCTP), a RNase inhibitor, and DEPC-treated water.

The method of the present invention may further include preparing a composition for a positive control to increase reliability in detection of coronavirus. The composition may be stored in a separate container from the above-described primer/probe mixture. The composition may be stored in a separate container from the above-described composition for performing real-time PCR.

Specifically, the composition for a positive control may include a plasmid containing RdRp gene of coronavirus, a plasmid containing N gene of coronavirus, a plasmid containing E gene of coronavirus, and a plasmid containing human RNase P gene. These plasmids having RdRp gene, N gene and E gene of coronavirus, and the human RNase P gene, respectively, may be prepared by a conventional method known in the art with.

The above-described composition for a positive control may further include a buffer (e.g., TE-buffer) conventionally used by those of ordinary skill in the art to store and maintain a plasmid.

The method of the present invention may further include preparing a composition for a negative control to increase reliability in the detection of coronavirus. The composition may be contained in a separate container from the above-described primer/probe mixture. The composition may be stored in a separate container from the above-described composition for performing real-time PCR or the composition for a positive control.

The composition for a negative control may include deionized water, but the present invention is not limited thereto.

A coronavirus diagnostic kit according to one embodiment of the present invention includes a first container containing the above-described primer/probe mixture.

The container may be a tube or another suitable ampoule.

The coronavirus diagnostic kit may include a second container containing the above-described composition for performing real-time PCR, a third container containing the above-described composition for a positive control, and a fourth container containing the above-described composition for a negative control.

The coronavirus diagnostic kit may be used to confirm whether a disease caused by coronavirus occurs in a patient, and provide information for diagnosing coronavirus. In addition, the coronavirus diagnostic kit may have high analytic specificity, analytic sensitivity, reproducibility and repetitiveness and no interference, and may be used to conveniently diagnose coronavirus.

The method of diagnosing coronavirus according to one embodiment of the present invention includes a method of diagnosing sample RNA using the coronavirus diagnostic kit according to one embodiment of the present invention.

More specifically, the method of diagnosing coronavirus includes performing reverse transcription and real-time PCR using the sample.

The "sample" used herein may be extracted from a respiratory tract suspected of coronavirus infection. For example, the sample may be an alveolar lavage fluid, a throat swab, sputum, or saliva, but the present invention is not limited thereto.

MODE FOR IMPLEMENTATION OF INVENTION

Hereinafter, the configuration and action of the present invention will be described in further detail through exemplary embodiments of the present invention. However, this is presented as a preferred example of the present invention and should not be construed as limiting the present invention in any sense.

Example 1

Preparation of Coronavirus-Specific Primers And Probes

Example 1-1

Preparation of Coronavirus-Specific Primers

The inventors prepared a primer pair having base sequences of SEQ ID NOs: 1 and 2, which amplify RdRp gene of coronavirus, a primer pair having base sequences of SEQ ID NOs: 3 and 4, which amplify N gene of coronavirus, a primer pair having base sequences of SEQ ID NOs: 5 and 6, which amplify E gene of coronavirus, by a conventional method. In addition, as internal control primers, a primer pair having base sequences of SEQ ID NOs: 7 and 8, which amplify human RNase P gene, was prepared by a conventional method.

TABLE 1

| Name | Base sequence (5'→3') | Length | SEQ ID NO: |
|---|---|---|---|
| B_RdRP_F1 | GTGAAATGGTCATGTGTGGCGG | 22 | 1 |
| B_RdRP_R1 | CAAATGTTAAAAACACTATTAGCATA | 26 | 2 |
| N_F | GGGGAACTTCTCCTGCTAGAAT | 22 | 3 |
| N_R | CAGACATTTTGCTCTCAAGCTG | 22 | 4 |
| B_E_F1 | ACAGGTACGTTAATAGTTAATAGCGT | 26 | 5 |
| B_E_R1 | ATATTGCAGCAGTACGCACACA | 22 | 6 |
| Rnase_F | AGATTTGGACCTGCGAGCG | 19 | 7 |
| Rnase_R | GAGCGGCTGTCTCCACAAGT | 20 | 8 |

Example 1-2 Preparation of Coronavirus-Specific Probes

The inventors prepared a probe having a base sequence of SEQ ID NO: 9 capable of detecting RdRp gene of coronavirus, a probe having a base sequence of SEQ ID NO: 10 capable of detecting N gene of coronavirus, a probe having a base sequence of SEQ ID NO: 11 capable of detecting E gene of coronavirus, and a probe having a base sequence of SEQ ID NO: 12 capable of detecting human RNase P gene by a conventional method.

TABLE 2

| Name | 5' | Base sequence (5'→3') | 3' | Length | SEQ ID NO: |
|---|---|---|---|---|---|
| B_RdRP_P2 | FAM | CAGGTGGAACCTCATCAGGAGATGC | SFCQ | 25 | 9 |
| N_P | JOE | TTGCTGCTGCTTGACAGATT | SFCQ | 20 | 10 |
| B_E_P1 | Texas Red | ACACTAGCCATCCTTACTGCGCTTCG | SFCQ | 26 | 11 |
| RnaseP_P | Cy5 | TTCTGACCTGAAGGCTCTGCGCG | SFCQ | 23 | 12 |

Example 2

Preparation of Primer/Probe Mixture

Each of the prepared primer pairs and probes in Tables 1 and 2 was added to a 50 mL tube at a content of 100 pmol per 1 μL of TE buffer and mixed, thereby preparing a single-component primer/probe mixture.

Example 3

Preparation of Composition for Positive Control and Composition for Negative Control

Example 3-1

Acquisition of Gene

Genetic information on the RdRp gene, N gene and E gene of coronavirus and the human RNase P gene was collected from the National Center for Biotechnology Information (NCBI) and GISAID. DNA was synthesized by confirming the DNA sequence for a specific amplification section considering a primer pair and probes to be used herein.

Example 3-2

Transformation

50 μL of TE buffer was added to a plasmid clone having the synthesized RdRp gene, N gene, E gene and RNase P gene, and the clone was completely suspended through vortexing for 1 minute. 2 μL (10 ng/μL) of each synthesized clone was added to 100 μL of Hit-DH5 alpha Competent cells (RBCs), gently tapped, and then maintained on ice for 5 minutes. A LB (ampicillin+) agar plate was prepared, and then 70 μL of a competent cell mixture containing each clone was spread with a spreader. Additionally, another LB (ampicillin+) agar plate was plated, and then 30 μL of a competent cell mixture containing each clone was spread with a spreader. These two agar plates were incubated at 37° C. for 18 hours. Among the two agar plates, colonies in which single colonies were well formed were selected, and the transformed colonies were selected again and then shake-cultured in LB broth for 16 hours.

Example 3-3

Preparation of Plasmid

The incubated culture solution was centrifuged at 10,000 g for 5 minutes, and then as much supernatant as possible was removed. 250 μL of buffer S1 (Exprep Plasmid SV mini; GeneAll, Korea) was added, vortexed and suspended, and then the resulting suspension was transferred to a new 1.5 mL tube. 250 μL of buffer S2 (Exprep Plasmid SV mini; GeneAll, Korea) was added, and inverted four times. 350 μL of buffer S3 (Exprep Plasmid SV mini; GeneAll, Korea) was added, and immediately inverted 4 to 6 times. The resulting product was centrifuged at 1,300 rpm for 10 minutes. The supernatant was carefully transferred to an SV column, and centrifuged for 30 seconds. After removing the SV column, the solution was discarded, and the SV column was installed again in a capture tube. After the addition of 700 μL of buffer PW (Exprep Plasmid SV mini; GeneAll, Korea) and centrifugation for 30 seconds, a solution obtained after removal of the SV column was discarded, and then the SV column was installed again in a capture tube. After 1-minute centrifugation to remove a remaining washing buffer, the SV column was transferred to a new 1.5 mL tube. 50 μL of buffer EB or deionized water was added, maintained for 1 minute, and then centrifuged for 1 minute, thereby preparing a plasmid.

Example 3-4

Preparation of Composition for Positive Control

A composition for a positive control was prepared by adding each of the prepared plasmids into a 50 mL of tube at a content of 10 ng per 1 μL of TE buffer and mixing.

Example 3-5

Preparation of Composition for Negative Control

A composition for a negative control was prepared by adding deionized water to a 50 mL tube.

Example 4

Manufacture of Coronavirus Diagnostic Kit

A diagnostic kit consisting of a total of four containers such as a first container containing the primer/probe mixture prepared in Example 1, a third container containing the composition for a positive control prepared in Example 3-4, a fourth container containing the composition for a negative control prepared in Example 3-5, and a second container containing the composition for real-time PCR containing a reverse transcriptase and dNTPs was manufactured.

Example 5

Method of Diagnosing Coronavirus

RNA was extracted from a sample using an RNA extraction kit (QIAamp Viral RNA mini kit, Qiagen, Germany). An RT-PCR master mixture was prepared by mixing 5 μL of the primer/probe mixture per 10 μL of the composition for real-time PCR. 15 μL of the prepared RT-PCR master mixture was dispensed into each well, and 5 μL of the extracted RNA was added to each well and mixed well. The composition for a positive control and the composition for a negative control were treated in the same manner as the primer/probe mixture.

A reaction was performed in a real-time PCR device. Specific PCR reaction conditions are shown in Table 3 below.

TABLE 3

| Temperature | Time | Cycle |
|---|---|---|
| 50° C. | 20 min | 1 cycle |
| 95° C. | 5 min | 1 cycle |
| 95° C. | 15 sec | 45 cycles |
| 58° C.* | 60 sec | |

Fluorescence scan in * step.

When PCR was conducted on the composition for a positive control and the composition for a negative control, the Ct value is shown in Table 4 below, and when the Ct value of each sample in each item is 35 or less, it was determined as positive.

| | FAM | Texas Red | JOE | Cy5 |
|---|---|---|---|---|
| Positive control | ≤40 | ≤40 | ≤40 | ≤35 |
| Negative control | No Ct | No Ct | No Ct | No Ct |

Experimental Example 1

Analytic Specificity

Real-time PCR was performed on viruses (obtained from the Korea National Research Resource Center (KNRRC) and the National Cancer Control Program (NCCP)) shown in Table 5 below using the coronavirus diagnostic kit prepared in example 4. Each DNA/RNA concentration was adjusted to 1 ng/μL, and the PCR was repeated three times. As a result, all viruses tested negative. Therefore, it can be confirmed that the coronavirus diagnostic kit of the present invention exhibits excellent analytic specificity for coronavirus.

TABLE 5

| No. | Virus Name |
|---|---|
| 1 | Influenza A (H1N1/09) |
| 2 | Influenza A (H3N2) |
| 3 | Influenza A (H5N1) |
| 4 | Influenza B |
| 5 | Rhinovirus |
| 6 | Respiratory syncytial virus (A/B) |
| 7 | Parainfluenza 1 virus |
| 8 | Parainfluenza 2 virus |
| 9 | Parainfluenza 3 virus |
| 10 | Parainfluenza 4 virus |
| 11 | Adenovirus |
| 12 | Human Bocavirus |
| 13 | Measles virus |
| 14 | *Mycoplasma* spp. |

Experimental Example 2

Analytic Sensitivity

A sensitivity test was performed using the obtained target RNA of coronavirus. The target RNA was prepared at various concentrations, and real-time PCR was performed thereon using the prepared coronavirus diagnostic kit. As a result, the calculated analytic sensitivity according to CLSI EP17-A was confirmed as 10 copies/reaction of the RdRp gene, E gene and N gene of coronavirus.

Experimental Example 3

Reproducibility

A coronavirus diagnostic kit was prepared in the same method as described in Example 4 on another day. And then, PCR was performed on target RNA of coronavirus at the same concentration by the same method. As a result, less than 5% CV was shown, indicating excellent reproducibility.

Experimental Example 4

Repeatability

Diagnosis was performed at the same concentrations of target RNAs of coronavirus with the diagnostic kit of Example 4 twice a day for 12 days. All diagnostic results were less than 5% CV, indicating excellent repeatability.

Experimental Example 5

Interference

As interfering substances, mucin, NaCl, blood, respiratory syncytial virus A, and 1×PBS were prepared. Each of the interfering substances was added to a sample obtained by a throat swab, and coronavirus RNA was extracted therefrom. As a result, regardless of an interfering substance, it was possible for coronavirus to test 100% positive.

Comparative Example 1

A virus diagnostic kit was manufactured by the same method as described in Example 4, except that a primer pair of SEQ ID NO: 13 (forward) and SEQ ID NO: 14 (reverse) (SEQ ID NO: 13: RdRp-1_F, SEQ ID NO: 14: RdRp-1_R) was used instead of the primer pair of SEQ ID NOs: 1 and 2 in Example 1. Evaluation was performed by the same methods as described in Experimental Examples 1 to 5 using the manufactured virus diagnostic kit. As a result, there was a problem that the sensitivity of the coronavirus RdRp gene is decreased.

Comparative Example 2

A virus diagnostic kit was manufactured by the same method as described in Example 4, except that a primer pair of SEQ ID NO: 15 (forward) and SEQ ID NO: 16 (reverse) (SEQ ID NO: 15: N-F-1, SEQ ID NO: 16: N-R-1) was used instead of the primer pair of SEQ ID NOs: 3 and 4 of Example 1. Evaluation was performed by the same methods as described in Experimental Examples 1 to 5 using the manufactured virus diagnostic kit. As a result, there was a problem that the sensitivity of the coronavirus N gene is decreased.

Comparative Example 3

A virus diagnostic kit was manufactured by the same method as described in Example 4, except that a primer pair of SEQ ID NO: 17 (forward) and SEQ ID NO: 18 (reverse) (SEQ ID NO: 17: E-F-1, SEQ ID NO: 18: E-R-2) was used instead of the primer pair of SEQ ID NOs: 5 and 6 of Example 1. Evaluation was performed by the same methods as described in Experimental Examples 1 to 5 using the manufactured virus diagnostic kit. As a result, there was a problem that the sensitivity of the coronavirus E gene is decreased.

Base sequences of the primer pairs used in Comparative Examples 1 to 3 are shown in Table 6 below.

TABLE 6

| Name | Base sequence (5'→3') | Length | SEQ ID NO: |
|---|---|---|---|
| RdRp-1_F | GTGARATGGTCATGTGTGGCGG | 22 | 13 |
| RdRp-1_R | CARATGTTAAASACACTATTAGCATA | 26 | 14 |
| N-F-1 | GGGGAACTTCTCCTGCTAGA | 20 | 15 |
| N-R-1 | GACATTTTGCTCTCAAGCTG | 20 | 16 |
| E-F-1 | CAGGTACGTTAATAGTTAATAGCGT | 25 | 17 |
| E-R-2 | ATATTGCAGCAGTACGCACAC | 21 | 18 |

As above, the present invention was described with reference to examples. It will be understood by those of ordinary skill in the art that the present invention can be implemented in modified forms without departing from the essential features of the present invention. Therefore, the disclosed embodiments should be considered in a descriptive aspect, rather than a limiting aspect. The scope of the present invention is shown in the claims rather than the foregoing description, and all differences within the equivalent range thereto will be construed as being included in the present invention.

The invention claimed is:

1. A method of manufacturing a coronavirus diagnostic kit, the method comprising:
    preparing a one-component primer/probe mixture by mixing:
        a primer set including a primer pair consisting of base sequences of SEQ ID NOs: 1 and 2, a primer pair consisting of base sequences of SEQ ID NOs: 3 and 4, a primer pair consisting of base sequences of SEQ ID NOs: 5 and 6, and a primer pair consisting of base sequences of SEQ ID NOs: 7 and 8; and
        a probe consisting of a base sequence of SEQ ID NO: 9, a probe consisting of a base sequence of SEQ ID NO: 10, a probe consisting of a base sequence of SEQ ID NO: 11, and a probe consisting of a base sequence of SEQ ID NO: 12.

2. The method of claim 1, further comprising:
    preparing a composition which includes a plasmid containing RdRp gene of the coronavirus, a plasm id containing N gene of the coronavirus, a plasm id containing E gene of the coronavirus, and a plasmid containing human RNase P gene.

3. The method of claim 2, wherein the one-component primer/probe mixture is prepared in a separate container from the composition containing the plasm ids.

4. The method of claim 1, wherein the coronavirus diagnostic kit manufactured by the method is used for real-time polymerase chain reaction (PCR).

5. A coronavirus diagnostic kit, which is manufactured by the method of claim 1.

6. A method of diagnosing a coronavirus infection, the method comprising:
    diagnosing the coronavirus infection using the coronavirus diagnostic kit of claim 5.

* * * * *

SEQUENCE LISTING

<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: B_RdRP_F1 FORWARD PRIMER

<400> SEQUENCE: 1
gtgaaatggt catgtgtggc gg          22

<210> SEQ ID NO 2
<211> LENGTH: 26
<212> TYPE: DNA

```
<213> ORGANISM: Artificial Sequence
<220> FEATURE:
<223> OTHER INFORMATION: B_RdRP_R1 REVERSE PRIMER

<400> SEQUENCE: 2
caaatgttaa aaacactatt agcata                                          26

<210> SEQ ID NO 3
<211> LENGTH: 22
<212> TYPE: DNA
<213> ORGANISM: Artificial Sequence
<220> FEATURE:
<223> OTHER INFORMATION: N_F FORWARD PRIMER

<400> SEQUENCE: 3
ggggaacttc tcctgctaga at                                              22

<210> SEQ ID NO 4
<211> LENGTH: 22
<212> TYPE: DNA
<213> ORGANISM: Artificial Sequence
<220> FEATURE:
<223> OTHER INFORMATION: N_R REVERSE PRIMER

<400> SEQUENCE: 4
cagacatttt gctctcaagc tg                                              22

<210> SEQ ID NO 5
<211> LENGTH: 26
<212> TYPE: DNA
<213> ORGANISM: Artificial Sequence
<220> FEATURE:
<223> OTHER INFORMATION: B_E_F1 FORWARD PRIMER

<400> SEQUENCE: 5
acaggtacgt taatagttaa tagcgt                                          26

<210> SEQ ID NO 6
<211> LENGTH: 22
<212> TYPE: DNA
<213> ORGANISM: Artificial Sequence
<220> FEATURE:
<223> OTHER INFORMATION: B_E_R1 REVERSE PRIMER

<400> SEQUENCE: 6
atattgcagc agtacgcaca ca                                              22

<210> SEQ ID NO 7
<211> LENGTH: 19
<212> TYPE: DNA
<213> ORGANISM: Artificial Sequence
<220> FEATURE:
<223> OTHER INFORMATION: Rnase_F FORWARD PRIMER

<400> SEQUENCE: 7
agatttggac ctgcgagcg                                                  19

<210> SEQ ID NO 8
<211> LENGTH: 20
<212> TYPE: DNA
<213> ORGANISM: Artificial Sequence
<220> FEATURE:
<223> OTHER INFORMATION: Rnase_R REVERSE PRIMER

<400> SEQUENCE: 8
gagcggctgt ctccacaagt                                                 20
```

<210> SEQ ID NO 9
<211> LENGTH: 25
<212> TYPE: DNA
<213> ORGANISM: Artificial Sequence
<220> FEATURE:
<223> OTHER INFORMATION: B_RdRP_P2 PROBE

<400> SEQUENCE: 9
caggtggaac ctcatcagga gatgc                                          25

<210> SEQ ID NO 10
<211> LENGTH: 20
<212> TYPE: DNA
<213> ORGANISM: Artificial Sequence
<220> FEATURE:
<223> OTHER INFORMATION: N_P PROBE

<400> SEQUENCE: 10
ttgctgctgc ttgacagatt                                                20

<210> SEQ ID NO 11
<211> LENGTH: 26
<212> TYPE: DNA
<213> ORGANISM: Artificial Sequence
<220> FEATURE:
<223> OTHER INFORMATION: B_E_P1 PROBE

<400> SEQUENCE: 11
acactagcca tccttactgc gcttcg                                         26

<210> SEQ ID NO 12
<211> LENGTH: 23
<212> TYPE: DNA
<213> ORGANISM: Artificial Sequence
<220> FEATURE:
<223> OTHER INFORMATION: RnaseP_P PROBE

<400> SEQUENCE: 12
ttctgacctg aaggctctgc gcg                                            23

<210> SEQ ID NO 13
<211> LENGTH: 22
<212> TYPE: DNA
<213> ORGANISM: Artificial Sequence
<220> FEATURE:
<223> OTHER INFORMATION: RdRp-1_F FORWARD PRIMER

<400> SEQUENCE: 13
gtgaratggt catgtgtggc gg                                             22

<210> SEQ ID NO 14
<211> LENGTH: 26
<212> TYPE: DNA
<213> ORGANISM: Artificial Sequence
<220> FEATURE:
<223> OTHER INFORMATION: RdRp-1_R REVERSE PRIMER

<400> SEQUENCE: 14
caratgttaa asacactatt agcata                                         26

<210> SEQ ID NO 15
<211> LENGTH: 20
<212> TYPE: DNA
<213> ORGANISM: Artificial Sequence
<220> FEATURE:

```
<223> OTHER INFORMATION: N-F-1 FORWARD PRIMER

<400> SEQUENCE: 15
ggggaacttc tcctgctaga                                         20

<210> SEQ ID NO 16
<211> LENGTH: 20
<212> TYPE: DNA
<213> ORGANISM: Artificial Sequence
<220> FEATURE:
<223> OTHER INFORMATION: N-R-1 REVERSE PRIMER

<400> SEQUENCE: 16
gacattttgc tctcaagctg                                         20

<210> SEQ ID NO 17
<211> LENGTH: 25
<212> TYPE: DNA
<213> ORGANISM: Artificial Sequence
<220> FEATURE:
<223> OTHER INFORMATION: E-F-1 FORWARD PRIMER

<400> SEQUENCE: 17
caggtacgtt aatagttaat agcgt                                   25

<210> SEQ ID NO 18
<211> LENGTH: 21
<212> TYPE: DNA
<213> ORGANISM: Artificial Sequence
<220> FEATURE:
<223> OTHER INFORMATION: E-R-2 REVERSE PRIMER

<400> SEQUENCE: 18
atattgcagc agtacgcaca c                                       21
```